United States Patent [19]

Lunsford et al.

[11] Patent Number: 5,254,778
[45] Date of Patent: Oct. 19, 1993

[54] LITHIUM/MAGNESIUM OXIDE CATALYST AND METHOD OF MAKING

[75] Inventors: Jack H. Lunsford, Bryan; Paul G. Hinson, College Station, both of Tex.

[73] Assignee: The Texas A & M University System, College Station, Tex.

[21] Appl. No.: 711,210

[22] Filed: Jun. 6, 1991

Related U.S. Application Data

[62] Division of Ser. No. 483,357, Feb. 22, 1990, Pat. No. 5,041,405.

[51] Int. Cl.$^5$ .............................................. C07C 2/00
[52] U.S. Cl. .................................... 585/500; 585/943; 585/700; 585/541; 585/530; 585/520; 585/654; 585/656; 585/658
[58] Field of Search ............... 585/500, 943, 700, 541, 585/530, 520, 654, 656, 658

[56] References Cited

U.S. PATENT DOCUMENTS 2,627,506  2/1953  Hunter et al. .
4,450,310  5/1984  Fox et al. .
4,455,389  6/1984  Lewis et al. .
4,754,093  6/1988  Jezl et al. .
4,780,449  10/1988  Hicks .
4,826,796  5/1989  Erekson et al. .

FOREIGN PATENT DOCUMENTS 0205765  12/1986  European Pat. Off. .

*Primary Examiner*—Patrick P. Garvin
*Assistant Examiner*—E. D. Irzinski
*Attorney, Agent, or Firm*—Arnold, White & Durkee

[57] ABSTRACT

An improved method for preparing a catalyst which is superior for converting methane to ethane and ethylene is described. The method involves mixing a solution of a magnesium alkoxide in alcohol with a solution of a lithium compound in alcohol. Preferably, chlorine is introduced into the mixture. A solution of an aluminum alkoxide in an alcohol may also be added to the mixture. The magnesium alkoxide is hydrolyzed to produce a gel, and the gel is then calcined to produce the catalyst. Catalysts prepared by this method are superior for converting methane to ethane and ethylene, and have superior selectivities for ethylene and ethane over conventional lithium carbonate/magnesium oxide catalysts.

7 Claims, No Drawings

LITHIUM/MAGNESIUM OXIDE CATALYST AND METHOD OF MAKING

This is a divisional of application Ser. No. 07/483,357, filed Feb. 22, 1990, now U.S. Pat. No. 5,041,405.

BACKGROUND OF THE INVENTION

The invention relates to an improved lithium-magnesium oxide catalyst for converting methane to ethane and ethylene, and the method of making the catalyst. Specifically, the catalyst is made using a sol-gelling preparation technique. A solution of a magnesium alkoxide in an alcohol is prepared. The magnesium alkoxide solution is then mixed with a solution of a lithium compound in an alcohol. Preferably, chlorine is introduced to the mixture. The magnesium alkoxide in the mixture is hydrolyzed to form a gel, and the gel is then calcined to generate the solid catalyst. A catalyst prepared by this method achieves a greater conversion and superior selectivity at lower temperatures than conventional catalysts used for converting methane to ethane and ethylene.

Methane and ethane are readily available chemical feedstocks. They derive from various sources such as natural gas, anaerobic digestion of organic material, and as byproducts of many chemical processes. Methane and ethane are low molecular weight alkanes which exhibit high chemical stability. Because of their high chemical stability they are difficult to convert into higher molecular weight hydrocarbons. Moreover, it is difficult to convert ethane into ethylene.

In particular, it is desirable to convert methane and ethane to ethylene. Ethylene, unlike methane and ethane, is readily converted into higher molecular weight hydrocarbons. For example, ethylene is useful in synthesizing numerous other materials such as plastics. Consequently, there is a great desire to develop processes for converting readily available methane and ethane to more desirable hydrocarbons such as ethylene.

Substantial amounts of research have been conducted on catalytic processes for converting methane and ethane to higher molecular weight hydrocarbons. Keller et al. 73 JOURNAL OF CATALYSIS 9-19 (1982). For example, U.S. Pat. No. 4,826,796 teaches a catalyst for oxidative coupling of methane to produce ethane and ethylene. (Column 2, lines 5-12). Specifically, the patent describes a metal oxide catalyst which has the formula: $A_xB_yC_zO_q$ where A is an alkali metal selected from lithium, sodium, potassium, rubidium, and cesium; B is a cation which has an ionization state one greater than the ionization state of C, and B is selected from the group consisting of boron, aluminum, yttrium, and lanthanum; C is selected from the group consisting of magnesium, calcium, barium, and zinc; and O is oxygen. Z is 1, X ranges from 0.001-0.25, Y ranges from 0.01-0.25, and Q is the number necessary to maintain charge balance for the oxygen. (Claim 1 at column 6, lines 2-35). Metal oxide catalysts of these formulas provided conversions of up to 21.7 percent. (Table 1 at column 5, lines 10-25).

Conventional technology for converting methane has achieved ethane plus ethylene yields of only 20 weight percent. This yield is too low for economical commercial processes. In particular, a need exists for improved catalysts to convert methane and ethane selectively to ethylene at yields that are commercially feasible.

SUMMARY OF THE INVENTION

The invention comprises a sol-gelling method for preparing catalysts which are effective for converting methane to ethane and ethylene, and the catalysts produced by this method. The method comprises mixing a solution of a magnesium alkoxide dissolved in an alcohol with a solution of a lithium compound dissolved in an alcohol. Preferably, chlorine is added to the mixture. The magnesium alkoxide is hydrolyzed to form a gel. The gel is calcined to form the solid catalyst material, and the catalyst material is broken into particles and screened to achieve the appropriate size of catalyst particles.

The magnesium alkoxide solution is prepared by reacting magnesium metal with an alcohol. Chlorine can be included in the catalyst by using a chlorine compound to catalyze the reaction between the magnesium metal and alcohol. This produces a concentration of chlorine in the catalyst. Aluminum may also be included in the catalyst by mixing an aluminum alkoxide dissolved in an alcohol with the magnesium alkoxide solution.

Catalysts prepared by this method achieve superior results over catalysts prepared by conventional methods. Specifically, catalysts prepared by the sol-gel method provide higher conversions of methane at lower temperatures than conventional lithium carbonate/magnesium oxide catalysts. Further, catalysts prepared by the sol-gel method are more selective for the conversion of methane to ethylene and for the conversion of ethane to ethylene than conventional lithium carbonate/magnesium oxide catalysts.

DETAILED DESCRIPTION OF THE INVENTION

The invention provides improved lithium/magnesium oxide catalysts for the conversion of methane to ethane and ethylene. The catalyst is prepared using a sol-gelling preparation technique from metal alkoxides. Preferably, chlorine is included in the catalyst. Further, aluminum may be included in the catalyst.

The catalyst composition comprises lithium ions (Li+) and magnesium oxide (MgO). The reaction mechanism for converting methane to ethane and ethylene consists first of the oxidative dimerization of methane to ethane. Then the ethane is sequentially dehydrogenated to ethylene. The reaction is typically carried out at relatively low temperatures (less than 700° C.). At these temperatures, the dehydrogenation of ethane to ethylene is largely catalytic.

The Li+/MgO catalyst is prepared using a sol-gel method. First, a magnesium alkoxide is prepared as a solution in the corresponding alcohol. For example, magnesium 3-methyl-1-butoxide is prepared in 3-methyl-1-butanol. The magnesium alkoxide is prepared by reacting magnesium metal with the alcohol that corresponds to the desired alkoxide form. For example, to produce magnesium 3-methyl-1-butoxide, magnesium metal would be reacted with 3-methyl-1-butanol. To encourage the reaction between the magnesium metal and alcohol a catalyst is added. For example, carbon tetrachloride and a trace of mercuric chloride may be added to the magnesium metal and alcohol to catalyze the reaction forming the magnesium alkoxide. In addition, the use of a chlorine containing catalyst to form the magnesium alkoxide insures that chlorine is included in the final catalyst.

A solution of lithium nitrate dissolved in an alcohol such as ethanol is then slowly added to the magnesium alkoxide solution. The lithium is present in its ionic form ($Li^+$) in the alcohol. The solution is hydrolyzed with water, either from the atmosphere or by a water-saturated stream of nitrogen. This produces a gel. The mixture is then heated to evaporate the excess alcohols and to complete the gelling process. The gelled material is then calcined at elevated temperatures of approximately 700° C. The resulting solid material is then broken into smaller pieces using conventional means and sieved to the proper size range for use as a catalyst. Preferably, the catalyst particles range in size from particles that will pass a 20 mesh screen to particles that will be retained by a 42 mesh screen.

The use of a chlorine compound to catalyze the reaction between magnesium metal and the alcohol also generates concentrations of chlorine in the magnesium alkoxide solution. This produces concentrations of chlorine in the final catalyst.

Aluminum may also be included in the catalyst. This is accomplished by preparing a solution of aluminum alkoxide in a corresponding alcohol and adding the aluminum alkoxide solution to the magnesium alkoxide solution. For example, aluminum secbutoxide can be dissolved in sec-butanol and then slowly added to a magnesium alkoxide solution. Other metals could likewise be included in the catalyst by adding the appropriate metal alkoxide in an alcohol solution to the magnesium alkoxide solution.

EXAMPLE 1

Catalyst was prepared using the sol-gelling procedure. First, magnesium 3-methyl-1-butoxide was prepared from magnesium metal and 3-methyl-1-butanol (isoamyl alcohol). The reaction between the magnesium metal and isoamyl alcohol was catalyzed by carbon tetrachloride and a trace of mercuric chloride. This reaction produced a solution of magnesium 3-methyl-1-butoxide in 3-methyl-1-butanol which also contained chlorine.

An amount of an aluminum sec-butoxide solution which contained 6 grams of aluminum sec-butoxide, obtained from a commercial source, in 16 milliliters of sec-butanol was dripped into an amount of the magnesium 3-methyl-1-butoxide solution which contained 33 grams of magnesium 3-methyl-1-butoxide in 100 milliliters of 3-methyl-1-butanol under a nitrogen atmosphere. A solution of 3.7 grams of lithium nitrate dissolved in 50 milliliters of absolute ethanol was prepared, and the solution was added slowly to the mixture of the solutions of magnesium 3-methyl-1-butoxide and aluminum sec-butoxide. This produced a clear mixture which was maintained at 90° C. for several hours.

The alcohols were partially evaporated from the clear mixture by placing the mixture on a hot plate for 2 hours. The mixture was then allowed to stand open to the atmosphere for 2-3 days at room temperature, and during this period the mixture gelled. The gelled material was dried in an oven at 120° C. for 20 hours to further evaporate the alcohols.

The final gelled material was then calcined in an alumina crucible using the following temperature profile:

5° C. per minute to 500° C. and hold for 5 hours

3° C. per minute to 750° C. and hold for 10 hours The resulting calcined material was then pressed and sieved to form catalyst particles that passed through a 20 mesh screen but were retained by a 42 mesh screen.

The catalyst particles had a nominal composition, excluding chlorine, of $(Li_2O)_{0.16}(MgO)_1(Al_2O_3)_{0.073}$ based on the amounts of the starting materials used to prepare the catalyst.

An experiment was conducted to test the effectiveness of the catalyst particles for converting methane. Four grams of the catalyst particles were placed in a fused-quartz reactor having an inside diameter of 22 mm. The reactor was heated to the desired reaction temperature of 630° C. or 650° C. The flow rate of the reactor feed gas was 50 ml per minute. During the heat up the reactor feed gas was pure helium. When the desired reaction temperature was achieved, methane and oxygen, plus the helium diluent, were introduced over the catalyst at a flow rate of 50 ml per minute. The partial pressure of methane in the reactor feed gas was 66 Torr. The partial pressure of oxygen was 30 Torr.

Conversions and selectivities for this experiment are reported in Table 1.

TABLE 1

CATALYTIC PROPERTIES OF $Li^+/Al^{3+}/MgO$ FOR CONVERSION OF METHANE

| Time on Stream hrs | Temp °C. | CH$_4$ Conv % | % Selectivity | | | | Yield % |
|---|---|---|---|---|---|---|---|
| | | | C$_2$H$_4$ | C$_2$H$_6$ | CO$_2$ | CO | |
| 1.1 | 630 | 31.1 | 40.2 | 5.5 | 27.4 | 27.0 | 14.2 |
| 12.1 | 630 | 30.0 | 44.3 | 6.9 | 22.4 | 26.4 | 15.4 |
| 13.9 | 650 | 34.0 | 44.7 | 5.6 | 24.5 | 25.1 | 17.1 |
| 17.4 | 650 | 33.9 | 44.5 | 5.6 | 25.7 | 24.2 | 17.0 |
| 40.0 | 650 | 35.5 | 46.0 | 5.6 | 25.4 | 23.0 | 18.3 |

EXAMPLE 2

A second experiment was conducted to determine the effectiveness of the catalyst particles to convert ethane. The catalyst particles used for the second experiment were prepared in the same manner as the catalyst particles in the first experiment except they were not calcined at 750° C. Also the catalyst particles for the second experiment had previously been used to convert methane for 51 hours.

Two grams of catalyst particles were placed into a fused-quartz reactor having an inside diameter of 10 mm. The reactor was maintained at a temperature of about 600° C. with a maximum temperature of 625° C. The total flow rate for the reactor feed gas was 50 ml per minute. The partial pressure of ethane in the reactor feed gas was 103 Torr at times of 0.5 and 4.1 hours, and 101 Torr at times of 5.5, 9.3, and 20 hours. The partial pressure of oxygen in the reactor feed gas was 56 Torr at times of 0.5 and 4.1 hours, and 73 Torr at times of 5.5, 9 3, and 20 hours. The remainder of the reactor feed gas was helium.

Conversions and selectivities for the second experiment are reported in Table 2.

TABLE 2
CATALYTIC PROPERTIES OF $Li^+$—$Al^{+3}$—MgO FOR OXIDATIVE DEHYDROGENATION OF ETHANE AT 600° C.

| Time on Stream hrs | % Conversion | | % Selectivity | | | Yield % |
|---|---|---|---|---|---|---|
| | $C_2H_6$ | $O_2$ | $C_2H_4$ | CO | $CO_2$ | |
| 0.5 | 51 | 100 | 68 | 10 | 17 | 35 |
| 4.1 | 46 | 100 | 64 | 11 | 20 | 29 |
| 5.5 | 61 | 97 | 67 | 10 | 19 | 41 |
| 9.3 | 57 | 100 | 64 | 10 | 21 | 36 |
| 20 | 52 | 100 | 58 | 12 | 26 | 31 |

EXAMPLE 3

Catalyst particles were prepared using the procedure of Example 1. Specifically, a mixture of solutions of magnesium 3-methyl-1-butoxide, aluminum sec-butoxide, and lithium nitrate was prepared. Chlorine was introduced to the mixture by using carbon tetrachloride and mercuric chloride to catalyze the reaction between the magnesium metal and the 3-methyl-1-butanol. The mixture was dried to produce a gel, and the gel was calcined in air at 750° C. for 10 hours. The resulting calcined material was pressed and sieved to form catalyst particles that passed through a 20 mesh screen but were retained by a 42 mesh screen. The catalyst particles had a nominal composition of $(Li_2O)_{0.3}(MgO)_1(Al_2O_3)_{0.07}$, and contained 6 percent lithium by weight. In addition, the chlorine content of the catalyst particles was 21.8 percent by weight as determined by neutron activation analysis.

The catalyst was tested to determine its effectiveness for converting methane. Four grams of the catalyst particles were loaded into a fused-quartz reactor tube with an inside diameter of 22 mm. Otherwise, the experiment was carried out in a manner similar to Examples 1 and 2. The conversions and selectivities for various temperatures and partial pressures of the reactant gases are reported in Table 3.

TABLE 3
CATALYTIC PROPERTIES OF $Li^+/Al^{+3}/MgO$ FOR METHANE OXIDATION

| Time on Stream hrs | Temp °C. | $CH_4$ Conv % | % Selectivity | | | | Yield % |
|---|---|---|---|---|---|---|---|
| | | | $C_2H_4$ | $C_2H_6$ | $CO_2$ | CO | |
| Partial Pressure Methane/Oxygen = 66 Torr/30 Torr: | | | | | | | |
| 1.0 | 650 | 34.0 | 40.0 | 4.2 | 33.8 | 22.0 | 15.0 |
| 3.2 | 650 | 32.9 | 35.6 | 4.3 | 38.4 | 21.6 | 13.3 |
| 11.3 | 650 | 33.0 | 36.0 | 5.1 | 39.6 | 18.6 | 13.8 |
| 17.4 | 650 | 33.2 | 35.7 | 4.8 | 41.4 | 18.1 | 13.5 |
| 23.6 | 650 | 33.2 | 36.7 | 5.1 | 39.4 | 18.8 | 13.9 |
| Partial Pressure Methane/Oxygen = 74 Torr/31 Torr: | | | | | | | |
| 27.2 | 675 | 34.3 | 38.3 | 4.0 | 38.9 | 18.8 | 14.5 |
| 34.8 | 675 | 33.7 | 38.1 | 4.5 | 39.8 | 17.6 | 14.4 |
| 42.4 | 675 | 33.6 | 39.0 | 4.2 | 39.4 | 17.3 | 14.5 |
| Partial Pressure Methane/Oxygen = 126 Torr/52 Torr: | | | | | | | |
| 57.2 | 675 | 36.0 | 39.5 | 5.2 | 36.7 | 15.9 | 16.1 |
| 67.2 | 675 | 34.8 | 36.4 | 5.5 | 39.0 | 16.6 | 14.6 |
| 76.0 | 675 | 34.6 | 35.7 | 5.2 | 38.6 | 18.0 | 14.1 |
| 86.8 | 675 | 35.0 | 36.3 | 5.4 | 37.3 | 18.2 | 14.6 |
| 91.8 | 675 | 35.7 | 35.4 | 5.2 | 36.9 | 19.3 | 14.5 |

The experiment was continued for 92 hours before being shut down. Table 3 indicates that large ethylene to ethane ratios on the order of 7–9 were achieved with the catalyst material. The ethylene to ethane ratios for a conventional lithium carbonate/magnesium oxide catalyst would be 1–2. Further the carbon monoxide/carbon dioxide ratios were large. The carbon monoxide/carbon dioxide ratios for conventional lithium carbonate magnesium oxide catalyst would be close to 0. The combined yield for ethylene and ethane are about the same as would be expected for conventional magnesium oxide catalysts for these conditions. In all cases the reaction was close to oxygen limited, and consequently the methane conversion did not increase substantially when the temperature was increased from 650° C. to 675° C.

Table 3 indicates that the conversion and selectivities did not substantially change over the 90 hour period of the experiment which is unlike most chlorine promoted catalysts. Typically the chlorine in chlorine promoted catalysts acts as a reactant and thus is rapidly depleted from the catalyst. The chlorine content of the catalyst particles after the experiment was 7.4 percent by weight as determined by neutron activation analysis. During this period, only 16.2 mmol of chlorine were lost from the catalyst; but the amount of ethylene produced was 96 mmol. Clearly, the chlorine was not involved stoichiometrically in the formation of the ethylene. A chain mechanism could account for this result, however.

EXAMPLE 4

Catalyst particles were prepared without aluminum to determine the role of the aluminum in the catalyst. The catalyst particles were prepared using the procedure of Example 1 but without the addition of the aluminum sec-butoxide solution. Four grams of the catalyst particles were loaded into a fused-quartz reactor with an inside diameter of 22 mm.

An experiment similar to the experiment of Example 3 was conducted to determine the conversion of methane and selectivities for ethane and ethylene at various temperatures and partial pressures of the reactant gases. The results of this study are reported in Table 4.

TABLE 4
CATALYTIC PROPERTIES OF $Li^+/MgO$ FOR METHANE OXIDATION

| Time on Stream hrs | Temp °C. | $CH_4$ Conv % | % Selectivity | | | | Yield % |
|---|---|---|---|---|---|---|---|
| | | | $C_2H_4$ | $C_2H_6$ | $CO_2$ | CO | |
| Partial Pressure Methane/Oxygen = 65 Torr/31 Torr: | | | | | | | |
| 1.3 | 625 | 21.0 | 52.3 | 11.8 | 36.0 | 0 | 13.4 |
| 5.9 | 625 | 20.0 | 47.1 | 11.8 | 41.0 | 0 | 11.9 |
| 9.1 | 625 | 20.0 | 46.2 | 11.8 | 42.0 | 0 | 11.6 |
| 14.4 | 625 | 20.0 | 45.4 | 11.5 | 43.1 | 0 | 11.3 |
| Partial Pressure Methane/Oxygen = 66 Torr/31 Torr: | | | | | | | |
| 15.7 | 650 | 25.0 | 52.1 | 8.7 | 39.7 | 0 | 15.1 |
| 19.2 | 650 | 25.0 | 51.5 | 8.7 | 39.8 | 0 | 14.8 |
| 24.4 | 650 | 30.0 | 50.2 | 7.8 | 27.9 | 14.2 | 17.2 |
| 37.6 | 650 | 31.0 | 48.3 | 7.1 | 29.9 | 14.6 | 17.0 |
| Partial Pressure Methane/Oxygen = 68 Torr/33 Torr: | | | | | | | |
| 53.6 | 650 | 32.0 | 48.3 | 7.3 | 29.1 | 15.4 | 18.1 |
| 65.3 | 650 | 33.0 | 46.9 | 6.8 | 30.3 | 16.0 | 17.6 |

The ethane and ethylene selectivities were substantially improved in this experiment. The ethylene to ethane ratio at 650° C. was about the same as was obtained for the catalyst particles with aluminum at 650° C. The reason for the increase in the combined ethane and ethylene yield after 20 hours is unknown. The surface area of the catalyst particles after the experiment was 0.56 meters$^2$ per gram.

EXAMPLE 5

The experiment of Example 4 was repeated to determine the reproducibility of the results. Conversions and selectivities for this experiment are reported in Table 5.

TABLE 5

CATALYTIC PROPERTIES OF Li+/MgO FOR METHANE OXIDATION

| Time on Stream hrs | Temp °C. | $CH_4$ Conv % | % Selectivity | | | | Yield % |
|---|---|---|---|---|---|---|---|
| | | | $C_2H_4$ | $C_2H_6$ | $CO_2$ | CO | |
| Reactor Feed Gas Flow Rate = 45 ml/min: | | | | | | | |
| Partial Pressure Methane/Oxygen = 67 Torr/33 Torr: | | | | | | | |
| 1.0 | 650 | 34.0 | 46.3 | 6.6 | 30.8 | 16.3 | 17.8 |
| Partial Pressure Methane/Oxygen = 64 Torr/32 Torr: | | | | | | | |
| 9.0 | 650 | 35.0 | 44.1 | 6.4 | 34.9 | 14.4 | 17.6 |
| 16.4 | 650 | 33.0 | 44.5 | 7.3 | 34.6 | 13.6 | 17.1 |
| 19.8 | 650 | 35.0 | 45.1 | 6.55 | 33.8 | 14.8 | 18.3 |
| Reactor Feed Gas Flow Rate = 35 ml/min: | | | | | | | |
| Partial Pressure Methane/Oxygen = 75 Torr/34 Torr: | | | | | | | |
| 23.2 | 650 | 34.0 | 44.2 | 6.8 | 32.2 | 16.7 | 17.5 |
| 28.2 | 650 | 34.0 | 42.5 | 6.4 | 34.9 | 16.6 | 16.4 |
| Partial Pressure Methane/Oxygen = 67 Torr/34 Torr: | | | | | | | |
| 36.8 | 650 | 35.0 | 37.6 | 5.5 | 40.0 | 16.8 | 15.5 |
| Partial Pressure Methane/Oxygen = 320 Torr/152 Torr: | | | | | | | |
| 46.4 | 650 | 32.0 | 23.7 | 5.3 | 57.0 | 13.6 | 9.3 |
| Reactor Feed Gas Flow Rate = 56.8 ml/min: | | | | | | | |
| Partial Pressure Methane/Oxygen = 190 Torr/54 Torr: | | | | | | | |
| 48.7 | 650 | 23.0 | 38.5 | 12.4 | 37.9 | 9.8 | 11.9 |
| 56.3 | 650 | 23.0 | 36.8 | 12.0 | 37.9 | 11.0 | 11.4 |
| 61.3 | 650 | 23.0 | 35.1 | 11.9 | 39.2 | 11.6 | 10.9 |

The ethane and ethylene selectivities were somewhat less than obtained in Example 4 for catalyst particles after 24 hours, but the methane conversion was somewhat greater. Further, in this experiment the reactor outlet gases were bubbled through deionized water, and the deionized water was periodically tested for chlorine with silver nitrate. Only traces of chlorine were detected in the deionized water during the first 45 hours of the experiment, but much higher levels of chlorine were detected between 45 and 69 hours. It is important to note that the methane to oxygen ratio was increased during the 45 to 69 hour time period.

EXAMPLE 6

An experiment was conducted to explore the conversion of ethane to ethylene. Catalyst particles were prepared using the procedure of Example 1, but without including aluminum in the catalyst. Four grams of catalyst were loaded into a fused-quartz reactor and the catalyst particles were tested as in the examples described above. The conversions and selectivities for this experiment are reported in Table 6.

TABLE 6

CATALYTIC PROPERTIES OF Li+/MgO FOR OXIDATIVE DEHYDROGENATION OF ETHANE

| Temp °C. | Ratio $C_2H_6/O_2$ | $C_2H_6$ Conv % | % Selectivity | | | | Yield % |
|---|---|---|---|---|---|---|---|
| | | | CO | $CH_4$ | $CO_2$ | $C_2H_4$ | |
| Reactor Feed Gas Flow Rate = 49 ml/min: | | | | | | | |
| Partial Pressure Ethane = 69 Torr: | | | | | | | |
| 600 | 1.1 | 49.3 | 3.3 | — | 5.5 | 90.9 | 44.8 |
| 625 | 1.1 | 68.3 | 3.4 | 1.4 | 4.3 | 87.7 | 60.0 |
| 655 | 1.1 | 81.4 | 8.0 | 2.2 | 9.0 | 80.9 | 65.9 |
| 655 | 1.5 | 77.0 | 7.1 | 2.5 | 7.7 | 82.6 | 63.6 |
| 655 | 1.9 | 69.4 | 5.9 | 3.0 | 6.1 | 85.6 | 59.1 |
| 655 | 2.0 | 65.6 | 5.6 | 3.0 | 4.8 | 86.7 | 56.9 |
| 655 | 2.4 | 63.7 | 5.3 | 3.0 | 4.6 | 87.3 | 55.6 |

The ethylene yield of 66% at 655° C. using the Li+/Mg catalyst at a methane/oxygen ratio of 1/1 was substantially higher than a yield of about 30% which is achieved with conventional lithium carbonate/magnesium oxide catalysts at higher ethane partial pressures. This suggests that ethylene is being formed from ethane without the subsequent oxidation of ethylene. It should be appreciated that at the temperatures of the experiment gas phase oxidation of ethylene and ethane does not occur.

The examples and embodiments described above are illustrative of the invention. Changes and modifications can be made without departing from the scope of the invention. It is intended that such changes and modifications fall within the scope of the invention as defined by the appended claims. For example, the chlorine could be introduced to the catalyst before gelling occurs by introducing other chlorine compounds into the mixture of solutions.

What is claimed is:

1. An improved method for converting methane to ethane and ethylene comprising:
    preparing a catalyst, the method for preparation of the catalyst comprising:
        mixing a solution of a magnesium alkoxide in an alcohol with a solution of lithium ions in an alcohol;
        hydrolyzing the magnesium alkoxide in the solution to form a gel; and
        calcining the gel to form a catalyst which is effective for converting methane to ethane and ethylene; and
    contacting methane and oxygen with an effective amount of the catalyst at temperatures less than about 700° C. to convert part of the methane to ethane and ethylene.

2. The method of claim 1 wherein the temperature ranges from about 630° C. to about 650° C.

3. The method of claim 1 wherein the effective amount of the catalyst is about 1300 grams for a methane feed rate of 1 gram per minute.

4. An improved method for converting ethane to ethylene comprising:
    preparing a catalyst, the method for preparation of the catalyst comprising:
        mixing a solution of a magnesium alkoxide in an alcohol with a solution of lithium ions in an alcohol;
        hydrolyzing the magnesium alkoxide in the solution to form a gel;
        introducing an effective amount of chlorine to the catalyst to promote the activity of the catalyst for converting methane to ethane and ethylene; and
        calcining the gel to form a catalyst which is effective for converting methane to ethane and ethylene; and
    contacting ethane with an effective amount of the catalyst at temperatures less than 700° C. to convert part of the ethane to ethylene.

5. The method of claim 4 wherein the temperature ranges from about 630° C. to about 650° C.

6. The method of claim 4 wherein the effective amount of the catalyst is about 720 grams for an ethane feed rate of 1 gram per minute.

7. The method of claim 4 wherein the ratio of chlorine to lithium is greater than 0.85.

* * * * *